United States Patent
Tanaka et al.

(10) Patent No.: US 11,197,641 B2
(45) Date of Patent: Dec. 14, 2021

(54) COMMUNICATION DEVICE, ABNORMALITY NOTIFICATION SYSTEM, AND ABNORMALITY NOTIFICATION METHOD

(71) Applicant: PANASONIC INTELLECTUAL PROPERTY MANAGEMENT CO., LTD., Osaka (JP)

(72) Inventors: Toshiaki Tanaka, Hyogo (JP); Masaru Yamaoka, Osaka (JP); Kenji Masuda, Osaka (JP); Kazuhiro Watanabe, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 218 days.

(21) Appl. No.: 16/532,713

(22) Filed: Aug. 6, 2019

(65) Prior Publication Data

US 2019/0357857 A1    Nov. 28, 2019

Related U.S. Application Data

(63) Continuation of application No. PCT/JP2018/004354, filed on Feb. 8, 2018.

(30) Foreign Application Priority Data

Feb. 14, 2017    (JP) .............................. JP2017-024691

(51) Int. Cl.
*A61B 5/00* (2006.01)
*A61B 5/01* (2006.01)
(Continued)

(52) U.S. Cl.
CPC ............ *A61B 5/746* (2013.01); *A61B 5/0008* (2013.01); *A61B 5/0022* (2013.01);
(Continued)

(58) Field of Classification Search
CPC ... A61B 5/0008; A61B 5/0022; A61B 5/0075; A61B 5/0082; A61B 5/015; A61B 5/05;
(Continued)

(56) References Cited

U.S. PATENT DOCUMENTS

| 9,924,879 B2 * | 3/2018 | Van Den Heuvel ........................ A61B 5/02438 |
| 2008/0183049 A1 * | 7/2008 | Karkanias .............. G16H 40/67 600/301 |

(Continued)

FOREIGN PATENT DOCUMENTS

| CN | 104207755 A | 12/2014 |
| CN | 105662356 A | 6/2016 |

(Continued)

OTHER PUBLICATIONS

English Translation of Chinese Search Report dated Aug. 25, 2021 for related Chinese Patent Application No. 201880010359.3.

*Primary Examiner* — Quan-Zhen Wang
*Assistant Examiner* — Rajsheed O Black-Childress
(74) *Attorney, Agent, or Firm* — Greenblum & Bernstein, P.L.C.

(57) ABSTRACT

Communication device includes first sensor configured to measure a state of a sensing target person to acquire first measurement data, second sensor configured to measure a body temperature to acquire second measurement data, and memory unit configured to store a reference body temperature for a single or each of a plurality of predetermined states of the sensing target person. Communication device further includes state determiner configured to determine whether or not the sensing target person is in the single or any one of the plurality of predetermined states, and abnormality determiner configured to compare the reference body temperature with the body temperature of the sensing target person to (Continued)

determine whether or not the sensing target person has a body temperature abnormality.

19 Claims, 9 Drawing Sheets

(51) Int. Cl.
    *A61B 5/05*        (2021.01)
    *A61B 5/11*        (2006.01)

(52) U.S. Cl.
    CPC ............ *A61B 5/0082* (2013.01); *A61B 5/015* (2013.01); *A61B 5/05* (2013.01); *A61B 5/1115* (2013.01); *A61B 5/1118* (2013.01); *A61B 5/7275* (2013.01)

(58) Field of Classification Search
    CPC ....... A61B 5/11; A61B 5/1113; A61B 5/1115; A61B 5/1118; A61B 5/6889; A61B 5/6891; A61B 5/6892; A61B 5/7275; A61B 5/746
    See application file for complete search history.

(56) References Cited

U.S. PATENT DOCUMENTS

| | | |
|---|---|---|
| 2014/0275852 A1 | 9/2014 | Hong et al. |
| 2015/0119726 A1* | 4/2015 | Matsuno ............... A61B 5/1118 600/483 |
| 2018/0049677 A1* | 2/2018 | Marra ................... A61B 5/746 |
| 2018/0242887 A1* | 8/2018 | Dong ....................... A61B 5/11 |
| 2018/0338683 A1* | 11/2018 | Konno ................. A61B 5/0024 |
| 2020/0397379 A1* | 12/2020 | Franceschetti ........ A61B 5/1115 |

FOREIGN PATENT DOCUMENTS

| | | |
|---|---|---|
| CN | 105708440 A | 6/2016 |
| JP | 2004-049309 A | 2/2004 |
| JP | 2006-174919 A | 7/2006 |
| JP | 2008-217756 A | 9/2008 |

\* cited by examiner

| PERIOD | DETAILS OF NURSING CARE SERVICE |
|---|---|
| 2017/01/01/17:00 - 18:00 | BATHING SERVICE |
| 2017/01/02/15:00 - 16:00 | EXERCISING SERVICE |
| ... | ... |

COMMUNICATION DEVICE, ABNORMALITY NOTIFICATION SYSTEM, AND ABNORMALITY NOTIFICATION METHOD

CROSS-REFERENCE TO RELATED APPLICATIONS

This application is a continuation of the PCT International Application No. PCT/JP2018/004354 filed on Feb. 8, 2018, which claims the benefit of foreign priority of Japanese patent application No. 2017-024691 filed on Feb. 14, 2017, the contents all of which are incorporated herein by reference.

TECHNICAL FIELD

The present disclosure relates to a technique for abnormality notification to a sensing target person.

BACKGROUND ART

PTL 1 has an object of intuitively grasping a situation of a nursed person, and discloses storing a caricatured display image for each of a plurality of levels of vital data. There is then displayed a display image according to a level of the vital data on the nursed person acquired by a vital data acquisition unit.

PTL 2 discloses a technique of simultaneously detecting body temperature abnormality of a plurality of persons in accordance with a thermal image read by an infrared camera.

A person has body temperature rhythm of body temperature varying in one day. The body temperature rhythm thus needs to be taken into consideration for accurate detection of body temperature abnormality.

PTL 1 and PTL 2 each fail to take the body temperature rhythm of the sensing target person into consideration for accurate detection of body temperature abnormality.

CITATION LIST

Patent Literatures

PTL 1: Unexamined Japanese Patent Publication No. 2004-49309

PTL 2: Unexamined Japanese Patent Publication No. 2006-174919

SUMMARY OF THE INVENTION

The present disclosure provides a technique of accurately detecting body temperature abnormality of a sensing target person.

A communication device according to an aspect of the present disclosure is configured to notify of abnormality of a sensing target person, and includes a first sensor configured to measure a state of the sensing target person to acquire first measurement data, a second sensor configured to measure a body temperature of the sensing target person to acquire second measurement data, and a memory unit configured to store a reference body temperature for a single or each of a plurality of predetermined states of the sensing target person. The communication device further includes a state determiner configured to determine whether or not the sensing target person is in the single or any one of the plurality of predetermined states in accordance with the first measurement data acquired by the first sensor, and an abnormality determiner configured to compare the reference body temperature for the single or any one of the plurality of predetermined states with the body temperature of the sensing target person indicated by the second measurement data acquired by the second sensor, when the state determiner determines that the sensing target person is in the single or any one of the plurality of predetermined states. The abnormality determiner determines whether or not the sensing target person has a body temperature abnormality.

The abnormality determiner generates alerting information for abnormality notification when determining that the sensing target person has body temperature abnormality.

The present disclosure further provides an abnormality notification system configured to notify of abnormality of a sensing target person and including the communication device described above and a terminal device connected to the communication device via a network. The terminal device includes an output unit configured to output the alerting information generated by the abnormality determiner of the communication device.

The present disclosure provides an abnormality notification method with use of an abnormality notification system configured to notify of abnormality of a sensing target person. The abnormality notification method includes (a) measuring a state of the sensing target person with use of a first sensor to acquire first measurement data, and (b) measuring body temperature of the sensing target person with use of a second sensor to acquire second measurement data. The abnormality notification method further includes (c) determining whether or not the sensing target person is in a single or any one of a plurality of predetermined states in accordance with the first measurement data acquired by the first sensor, and (d) comparing reference body temperature for the single or any one of the plurality of predetermined states preliminarily stored in a memory unit with the body temperature of the sensing target person indicated by the second measurement data acquired by the second sensor when the sensing target person is determined as being in the predetermined state. The abnormality notification method includes accordingly determining whether or not the sensing target person has body temperature abnormality, (e) generating alerting information for abnormality notification, when the sensing target person is determined as having body temperature abnormality, and (f) outputting the generated alerting information.

The present disclosure achieves accurate detection of body temperature abnormality of a sensing target person.

Figure 1:
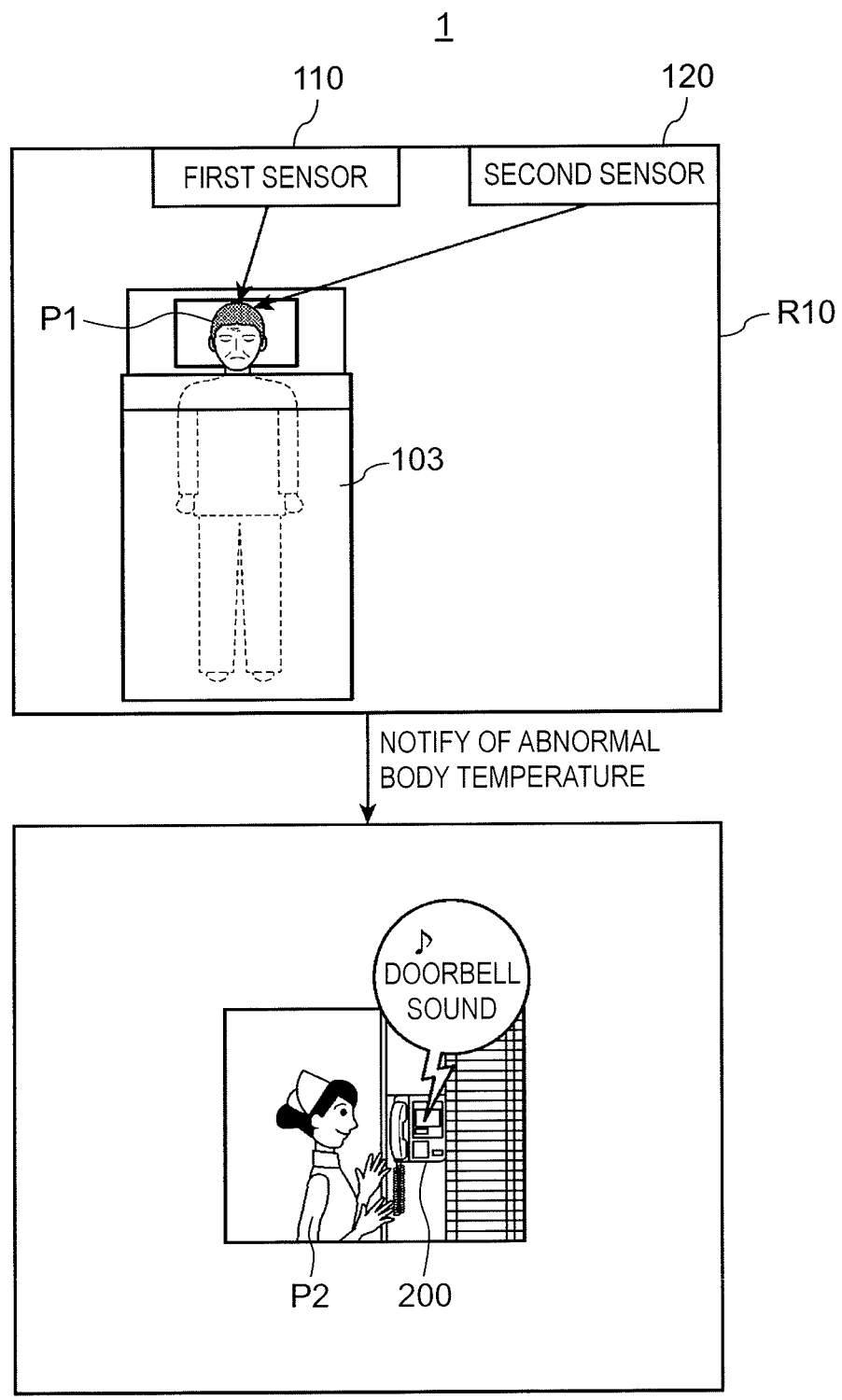
FIG. 1 is an explanatory diagram depicting a schematic configuration of an abnormality notification system according to a first exemplary embodiment of the present disclosure.

DESCRIPTION OF EMBODIMENTS (Developments of the Present Disclosure)

There has been recently developed a watching system configured to detect body movement of an elderly person with use of a radio wave sensor and watch behaviors of the elderly person. There has also been developed a body temperature sensor configured to contactlessly detect body temperature of a person with use of an infrared image sensor. Consideration has thus been given to incorporating such an infrared image sensor into a watching system to monitor body temperature of an elderly person.

Body temperature of a person varies in one day in accordance with states of the person such that the body temperature raises during active daytime and decreases during sleeping nighttime. It is accordingly important to consider body temperature variation according to states for accurate detection of body temperature abnormality of a person.

Both of the techniques disclosed in PTL 1 and PTL 2 are devised in no consideration of variation of body temperature according to states and fail to achieve accurate detection of body temperature abnormality of a sensing target person.

In view of this, the present disclosure provides a technique of accurately detecting body temperature abnormality of a sensing target person.

A communication device according to a first aspect of the present disclosure is configured to notify of abnormality of a sensing target person, and includes a first sensor configured to measure a state of the sensing target person to acquire first measurement data, a second sensor configured to measure a body temperature of the sensing target person to acquire second measurement data, and a memory unit configured to store a reference body temperature for a single or each of a plurality of predetermined states of the sensing target person. The communication device further includes a state determiner configured to determine whether or not the sensing target person is in the single or any one of the plurality of predetermined states in accordance with the first measurement data acquired by the first sensor, and an abnormality determiner configured to compare the reference body temperature for the single or any one of the plurality of predetermined states with the body temperature of the sensing target person indicated by the second measurement data acquired by the second sensor when the state determiner determines that the sensing target person is in the single or any one of the plurality of predetermined states, to determine whether or not the sensing target person has body temperature abnormality. The abnormality determiner generates alerting information for abnormality notification when determining that the sensing target person has body temperature abnormality.

The present aspect includes determining whether or not the sensing target person is in the single or any one of the plurality of predetermined states in accordance with the first measurement data measured by the first sensor. When the sensing target person is determined as being in the single or any one of the plurality of predetermined states, the reference body temperature for the single or any one of the plurality of predetermined states is compared with the body temperature indicated by the second measurement data measured by the second sensor to determine whether or not the sensing target person has body temperature abnormality. The present aspect thus achieves accurate detection of body temperature abnormality of the sensing target person in consideration of body temperature varying in accordance with states.

According to a second aspect, the first sensor and the second sensor in the aspect acquire the first measurement data and the second measurement data in a constant period, respectively. The communication device further includes a history data management unit configured to generate history data including the body temperature of the sensing target person acquired from the second measurement data and associated with the single or any one of the plurality of predetermined states, and accumulating the history data in the memory unit when the first measurement data acquired by the first sensor indicates that the sensing target person is in the single or any one of the plurality of predetermined states. The communication device further includes a reference body temperature management unit configured to analyze the history data, calculate the reference body temperature for single or any one of the plurality of predetermined states, and store the reference body temperature in the memory unit.

The present aspect includes further analyzing the history data associating the first measurement data and the second measurement data on the sensing target person to calculate the reference body temperature for the single or each of the plurality of predetermined states, and storing the reference body temperature in the memory unit. The present aspect thus achieves accurate detection of body temperature abnormality of the sensing target person in accordance with the reference body temperature appropriate for the sensing target person.

According to a third aspect, in the above aspect, the first sensor may be constituted by a radio wave sensor and the second sensor may be constituted by a thermal image sensor.

According to the present aspect, the first sensor is constituted by the radio wave sensor and is configured to contactlessly detect the state of the sensing target person. The second sensor is constituted by the thermal image sensor and is configured to contactlessly detect the body temperature of the sensing target person.

According to a fourth aspect, the first sensor in the above aspect may measure active mass of the sensing target person.

According to the present aspect, the active mass of the sensing target person is measured to achieve accurate detection of whether or not the sensing target person is in the predetermined state.

According to a fifth aspect, the state determiner in the above aspect may determine whether or not the sensing target person is in the single or any one of the plurality of predetermined states in accordance with the first measurement data and time of acquisition of the first measurement data.

The present aspect includes determining whether or not the sensing target person is in the single or any one of the plurality of predetermined states in further consideration of the time of acquisition of the first measurement data, to achieve more accurate detection of whether or not the sensing target person is in the single or any one of the plurality of predetermined states.

According to a sixth aspect, the reference body temperature management unit in the above aspect analyzes the history data, calculates normal body temperature of the sensing target person for each of the predetermined states as the reference body temperature, and stores the normal body temperature in the memory unit. The abnormality determiner may determine that the body temperature of the sensing target person has abnormality when the body temperature of the sensing target person measured by the second sensor is higher than the normal body temperature for the single or any one of the plurality of predetermined states by at least a certain degree.

The present aspect includes analyzing the history data on the sensing target person to calculate the normal body temperature of the sensing target person in the single or any one of the plurality of predetermined states and detect whether or not the sensing target person has body temperature abnormality with reference to the normal body temperature. This enables more accurate detection of body temperature abnormality of the sensing target person.

According to a seventh aspect, the state determiner in the above aspect detects whether or not the sensing target person is present in accordance with the first measurement data acquired by the first sensor. The abnormality determiner may start the second sensor only in a case where the state determiner detects presence of the sensing target person.

According to the present aspect, the second sensor is started only in the case where the sensing target person is present. This saves electricity consumption of the second sensor.

According to an eighth aspect, the state determiner in the above aspect detects whether or not the sensing target person is present in accordance with the first measurement data acquired by the first sensor. When the state determiner detects absence of the sensing target person and then detects presence of the sensing target person, the abnormality determiner does not need to determine whether or not the body temperature of the sensing target person has abnormality until a first period elapses after detection.

According to the present aspect, in an exemplary state where the sensing target person immediately after returning into a room has active mass larger than normal active mass, whether or not the body temperature of the sensing target person has abnormality is not determined to prevent erroneous detection of body temperature abnormality of the sensing target person.

According to a ninth aspect, the sensing target person corresponds to a nursed person subjected to a nursing care service in the above aspect. The communication device is connected, via a network, to a nursing care server configured to record a history of the nursing care service received by the nursed person. The abnormality determiner determines whether or not a second period has elapsed after the nursed person receives the nursing care service with reference to the history of the nursing care service, and does not need to determine whether or not the body temperature of the nursed person has abnormality until the second period elapses.

According to the present aspect, in an exemplary state where the sensing target person immediately after receiving the nursing care service has active mass larger than normal active mass, whether or not the sensing target person has body temperature abnormality is not determined to prevent erroneous detection of body temperature abnormality of the sensing target person.

According to a tenth aspect, the second sensor in the above aspect is constituted by a thermal image sensor configured to measure, as the first measurement data, thermal image data indicating temperature distribution in a measurement range around the second sensor. The memory unit preliminarily stores positional information indicating a position of the sensing target person staying in the measurement range. When presence of a plurality of persons in the measurement range is detected in accordance with the thermal image data, the abnormality determiner may compare coordinates of the persons in the thermal image data with the positional information to determine which one of the plurality of persons is the sensing target person.

The present aspect achieves accurate detection of body temperature abnormality of the sensing target person even in a case where a plurality of persons is present in the measurement range of the second sensor.

First Exemplary Embodiment

FIG. 1 is an explanatory diagram depicting a schematic configuration of abnormality notification system 1 according to the first exemplary embodiment of the present disclosure.

Abnormality notification system 1 includes first sensor 110, second sensor 120, and terminal device 200. First sensor 110 contactlessly detects a state of target person P1 as a sensing target. Second sensor 120 contactlessly detects body temperature of target person P1.

First sensor 110 and second sensor 120 may be installed in room R10 of target person P1. First sensor 110 and second sensor 120 may be incorporated in electrical equipment (e.g. an air conditioner) installed in room R10.

Room R10 is a habitable room of target person P1 in a facility like a retirement home or a hospital. Room R10 is equipped with bed 103 for target person P1. Room R10 may be a room alternatively located in a house of target person P1.

Abnormality notification system 1 determines whether or not target person P1 is in a specific state (a state immediately after rising is exemplarily adopted) in accordance with active mass detected by first sensor 110. Abnormality notification system 1 detects body temperature of target person P1 from data acquired by second sensor 120 when target person P1 is in the state immediately after rising. Abnormality notification system 1 compares the detected body temperature of target person P1 with preliminarily set normal body temperature of target person P1 in the state immediately after rising. Abnormality notification system 1 then determines whether or not target person P1 has body temperature abnormality (whether or not the body temperature and the normal body temperature of target person P1 are largely different from each other). If target person P1 has body temperature abnormality, abnormality notification system 1 generates alerting information and transmits the alerting information to terminal device 200.

Terminal device 200 may be disposed in a room of carer P2 (exemplifying a manager) who nurses target person P1 in the facility. Terminal device 200 having received the alerting information, outputs at least one of alerting sound and an alerting image to notify carer P2 of body temperature abnormality of target person P1. Carer P2 is thus promptly notified of body temperature abnormality of target person P1.

Figure 2:
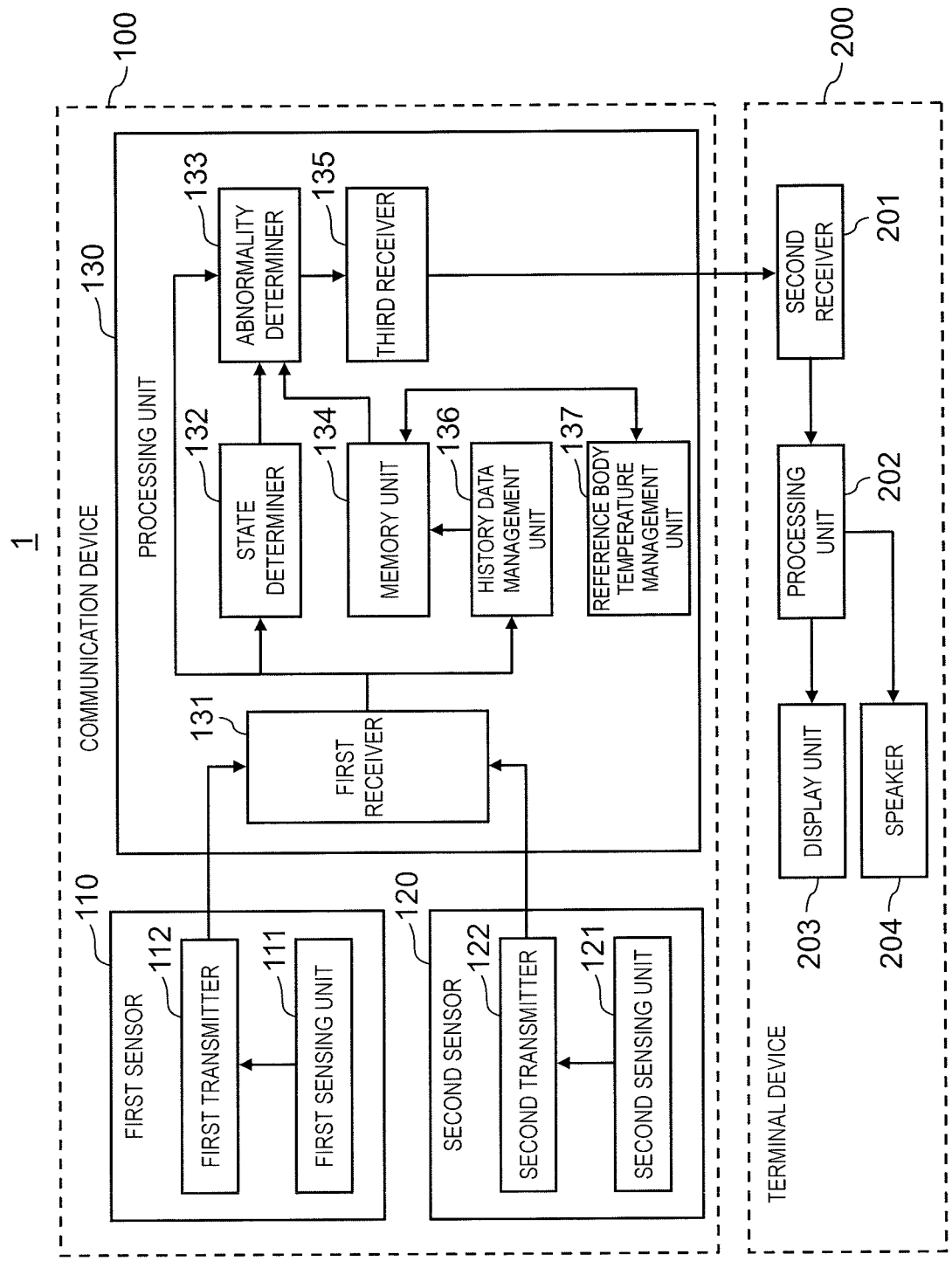
FIG. 2 is a block diagram depicting an entire configuration of the abnormality notification system according to the first exemplary embodiment of the present disclosure.

FIG. 2 is a block diagram depicting an entire configuration of abnormality notification system 1 according to the first exemplary embodiment. Abnormality notification system 1 includes communication device 100 and terminal device 200. Communication device 100 includes first sensor 110, second sensor 120, and processing unit 130.

Communication device 100 is exemplarily incorporated in the electrical equipment installed in room R10 as described above. Communication device 100 may alternatively be constituted by a dedicated device provided separately from the electrical equipment. Communication device 100 may still alternatively be constituted such that processing unit 130 is incorporated in the electrical equipment, and first sensor 110 and second sensor 120 are provided outside the electrical equipment. In this case, first sensor 110 and second sensor 120 may be disposed, for example, on a ceiling of room R10, at bed 103, or adjacent to bed 103. Communication device 100 includes constituent elements part or entirety of which may be constituted by a cloud server.

Terminal device 200 is constituted by a computer installed in the room of carer P2, and is communicably connected to communication device 100 via a network including at least one of a wireless local area network (LAN), a wired LAN, and a mobile phone communication network. Terminal device 200 may be constituted by a stationary computer or a mobile terminal such as a smartphone or a tablet terminal carried by carer P2. Terminal device 200 includes constituent elements part or entirety of which may be incorporated in a separate reporting device such as a nurse call system.

First sensor 110 measures a state or the like of target person P1 to acquire active mass data (exemplifying first measurement data). First sensor 110 includes first sensing unit 111 and first transmitter 112.

First sensing unit 111 applies, to target person P1, a radio wave containing a microwave in a 24 GHz band or the like, and receives a reflected wave from target person P1. First sensing unit 111 includes a radio wave sensor configured to detect frequency change (the Doppler effect) of the applied radio wave and the reflected wave caused in accordance with moving speed of target person P1, and acquire active mass data indicating active mass of target person P1 from the frequency change thus detected. First sensing unit 111 may adopt a system of detecting a target object other than the Doppler system. First sensing unit 111 may adopt a frequency modulated continuous wave (FMCW) system or the like.

First transmitter 112 transmits the active mass data acquired by first sensing unit 111 to processing unit 130 in a predetermined sampling period.

Second sensor 120 measures body temperature of target person P1. Second sensor 120 includes second sensing unit 121 and second transmitter 122. Second sensing unit 121 may be constituted by a thermal image sensor configured to measure, in a predetermined sampling period, thermal image data (exemplifying second measurement data) indicating temperature distribution in the measurement range. The sampling period of second sensing unit 121 may be equal to or different from the sampling period of first sensing unit 111. For easier description, the following will assume that these sampling periods are equal to each other. Second transmitter 122 transmits the thermal image data measured by second sensing unit 121 to processing unit 130 in a constant period.

First sensor 110 is installed in room R10 and is configured to apply a radio wave toward bed 103. Second sensor 120 is installed in room R10 such that the measurement range includes bed 103. Specific target person P1 as a measurement target is preliminarily provided with an identifier. First sensor 110 and second sensor 120 associate the active mass data and the thermal image data with the identifier and transmit the acquired data to processing unit 130. Even in a case where there is a plurality of target persons P1 as monitoring targets, processing unit 130 can identify specific target person P1 out of the plurality of target persons P1.

In a case where first sensor 110 and second sensor 120 are provided integrally with processing unit 130, first transmitter 112 and second transmitter 122 are each constituted by an input/output interface configured to communicate with a processor such as a central processing unit (CPU) constituting processing unit 130. In another case where first sensor 110 and second sensor 120 are provided separately from processing unit 130, first transmitter 112 and second transmitter 122 are each constituted by a communication circuit including at least one of a wireless LAN and a wired LAN.

Processing unit 130 is constituted by a computer including a processor such as a CPU and a memory, and includes first receiver 131, state determiner 132, abnormality determiner 133, memory unit 134, third transmitter 135, history data management unit 136, and reference body temperature management unit 137.

First receiver 131 receives the active mass data transmitted from first transmitter 112, and receives the thermal image data transmitted from second transmitter 122. In the case where first sensor 110 and second sensor 120 are provided integrally with processing unit 130, first receiver 131 is constituted by an input/output interface configured to communicate with first sensor 110 and second sensor 120. In the other case where first sensor 110 and second sensor 120 are provided separately from processing unit 130, first receiver 131 is constituted by a communication circuit including at least one of a wired LAN and a wireless LAN.

State determiner 132 determines whether or not target person P1 is in the specific state (exemplifying a predetermined state) in accordance with the active mass data measured by first sensor 110. Exemplarily adopted as the specific state is the state immediately after rising in this case. Examples of the specific state also include a sleeping state, an eating state, and a state immediately before resting.

State determiner 132 calculates feature quantity or the like from the active mass data, and determines that target person P1 is in the specific state if the calculated feature quantity is similar to preliminarily set feature quantity for the specific state. Adoptable examples of the feature quantity include a temporal variation pattern of a value acquired by substituting the active mass data for a predetermined function (e.g. a Cole formula).

When state determiner 132 determines that target person P1 is in the specific state, abnormality determiner 133 compares the normal body temperature (exemplifying reference body temperature) for the specific state with the body temperature of target person P1 indicated by the thermal image data measured by second sensor 120. Abnormality determiner 133 thus determines whether or not target person P1 has body temperature abnormality. Abnormality determiner 133 extracts a region indicating target person P1 from the thermal image data through image processing, and calculates a representative temperature value (e.g. an average value or a median) in the extracted region. Abnormality determiner 133 fixes body temperature for the calculated average temperature value in accordance with a body temperature conversion table or a body temperature conversion function preliminarily set and indicating relation between temperature and body temperature. Abnormality determiner 133 then calculates the fixed body temperature as body temperature of target person P1. Normal body temperature corresponds to body temperature of target person P1 in a normal state.

The body temperature conversion table or the body temperature conversion function may not be preliminarily set but may alternatively be fixed in accordance with a temperature measurement result of target person P1 while the system is in operation.

The body temperature conversion table or the body temperature conversion function may still alternatively be calibrated so as to be optimal for the target person in accordance with a preliminarily set function. For example, body temperature information measured with use of an axillary thermometer or the like may be combined with the thermal image data to generate a transfer function.

Abnormality determiner 133 reads normal body temperature immediately after rising as reference body temperature from memory unit 134, and determines that target person P1 has body temperature abnormality if the fixed body temperature of target person P1 is higher than the normal body temperature thus read by at least a certain degree. Adoptable examples of the certain degree include preliminarily set values such as 0.5 degrees, one degree, 1.5 degrees, and 2.0 degrees.

Abnormality determiner 133 generates alerting information to notify carer P2 for target person P1 of abnormality when determining that target person P1 has body temperature abnormality. The alerting information exemplarily includes the identifier for distinction of target person P1 from other target persons, and the body temperature.

The thermal image data may alternatively not be converted to body temperature of target person P1. For example, temperature of target object P1 may be acquired continuously and alerting information may be generated when the temperature exceeds a certain threshold. Instead of comparison with absolute temperature such as body temperature, body temperature abnormality may alternatively be determined through comparison between temperature in the normal state and relative temperature, such as whether or not the body temperature is higher than the temperature in the normal state by at least a certain degree.

Memory unit 134 may be constituted by a nonvolatile memory device, for example, and preliminarily stores the normal body temperature of target person P1 in the specific state.

Third transmitter 135 may be constituted by a communication circuit configured to communicate with terminal device 200. Third transmitter 135 transmits alerting information to terminal device 200 when abnormality determiner 133 determines that target person P1 has body temperature abnormality.

When the active mass data measured by first sensor 110 indicates that target person P1 is in the specific state, history data management unit 136 generates, as history data, the body temperature of target person P1 acquired from the thermal image data measured by second sensor 120, and accumulates the history data in memory unit 134. When state determiner 132 determines that the active mass data indicates target person P1 in the specific state, history data management unit 136 accumulates the body temperature of target person P1 fixed in accordance with the thermal image data by abnormality determiner 133, as history data in memory unit 134. Memory unit 134 thus accumulates body temperature of target person P1 in the specific state.

Reference body temperature management unit 137 analyzes the history data accumulated in memory unit 134 to calculate normal body temperature for the specific state and store the normal body temperature in memory unit 134. In a case where memory unit 134 accumulates history data for a certain period (e.g. one or two months), reference body temperature management unit 137 calculates an average value of body temperature values of target person P1 included in the accumulated history data and stores the calculated average value as normal body temperature of target person P1 in memory unit 134.

In this case, reference body temperature management unit 137 may calculate, as normal body temperature of target person P1, an average value of all body temperature values accumulated in memory unit 134, or may calculate, as normal body temperature of target person P1, an average value of body temperature values during a latest certain period.

Reference body temperature management unit 137 may calculate normal body temperature each time a certain period elapses. Alternatively, reference body temperature management unit 137 may initially calculate normal body temperature after a certain period elapses, and may later calculate normal body temperature each time body temperature values are accumulated in memory unit 134. Still alternatively, reference body temperature management unit 137 may calculate normal body temperature of target person P1 not in accordance with elapse of such a certain period but in accordance with accumulation of a certain number of history data in memory unit 134.

Terminal device 200 includes second receiver 201, processing unit 202, display unit 203, and speaker 204. Second receiver 201 may be constituted by a communication circuit configured to communicate with communication device 100, receives the alerting information transmitted from third transmitter 135, and transmits the alerting information to processing unit 202.

Processing unit 202 having acquired the alerting information from second receiver 201 causes display unit 203 to display the alerting information as the alerting image in order to notify carer P2 of body temperature abnormality of target person P1. Processing unit 202 having acquired the alerting information from second receiver 201 causes speaker 204 to output the alerting sound in order to notify carer P2 of body temperature abnormality of target person P1.

The alerting image includes a name and a face image of target person P1, as well as a message indicating body temperature abnormality. Adoptable examples of the alerting sound include alarm sound or a speech message on body temperature abnormality of target person P1.

Display unit 203 may be constituted by an organic electroluminescence (EL) panel or a liquid crystal panel, and is configured to display an alerting image. Speaker 204 is configured to output alerting sound.

Display unit 203 may display body temperature information for each target person, including biological information acquired by first sensor 110 and other sensing information acquired by at least one of a temperature and humidity sensor and an illuminance sensor.

Display unit 203 may constitute part of a nurse call system or a nursing care business system, and may be configured to display body temperature information along with other information on target person P1.

Figure 3:
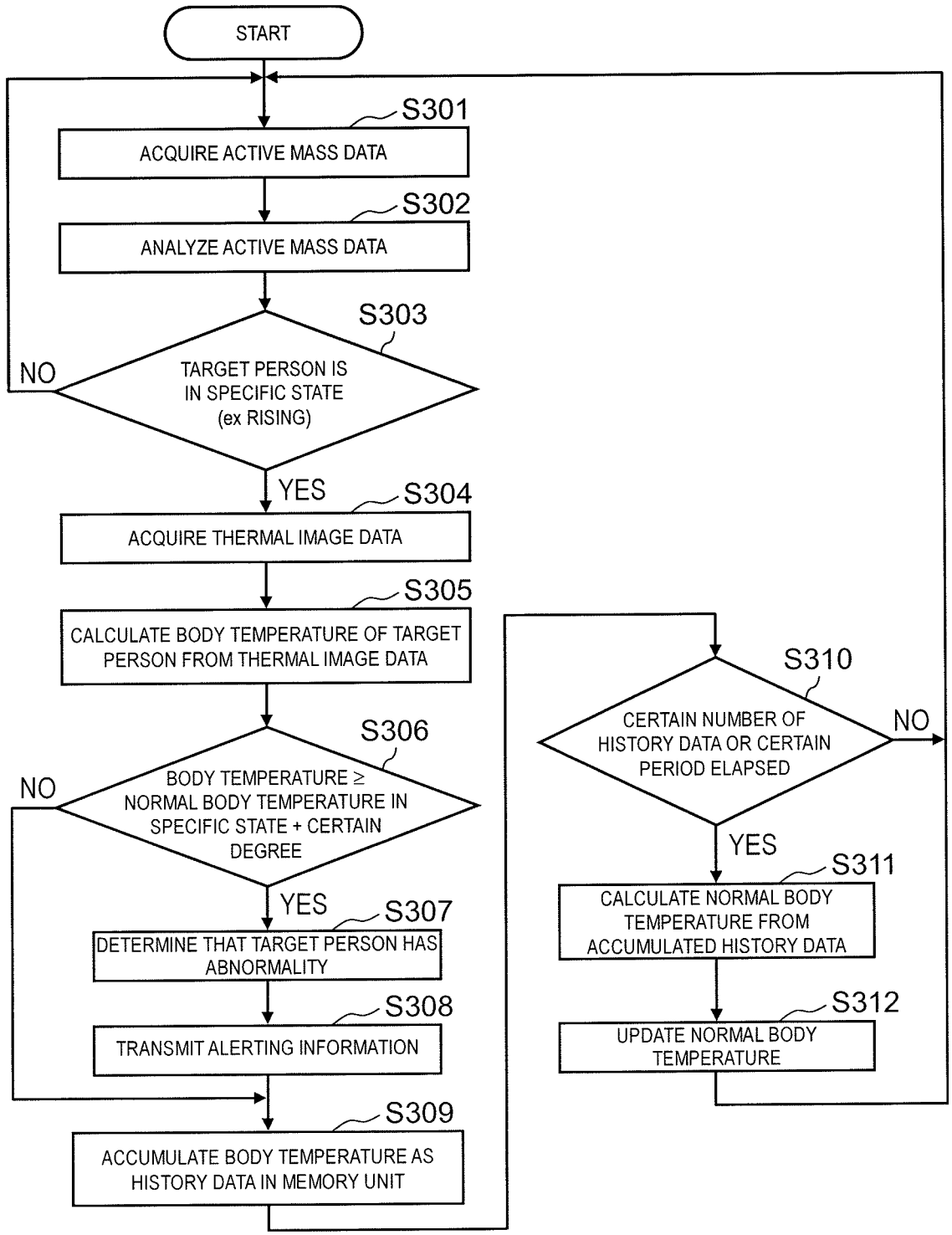
FIG. 3 is a flowchart depicting processing executed by the abnormality notification system according to the first exemplary embodiment of the present disclosure.

FIG. 3 is a flowchart depicting processing executed by abnormality notification system 1 according to the first exemplary embodiment. Assume that the processing in this flowchart is executed in a predetermined sampling period in the present exemplary embodiment.

State determiner 132 initially acquires latest active mass data measured by first sensor 110 (S301).

State determiner 132 subsequently analyzes the active mass data measured by first sensor 110 (S302). State determiner 132 then determines whether or not target person P1 is in the specific state (the state immediately after rising in this case) in accordance with an analysis result (S303). In a case where target person P1 is in the specific state (YES in S303), abnormality determiner 133 acquires latest thermal image data measured by second sensor 120 (S304). In another case where target person P1 is not in the specific state (NO in S303), the processing flow returns to step S301.

Abnormality determiner 133 subsequently calculates body temperature of target person P1 from the acquired thermal image data (S305).

Abnormality determiner 133 then determines whether or not the calculated body temperature is more than or equal to a value acquired by adding a certain degree to the normal body temperature in the specific state stored in memory unit 134 (S306). In a case where the calculated body temperature is more than or equal to the value acquired by adding the certain degree to the normal body temperature in the specific state stored in memory unit 134 (YES in S306), abnormality determiner 133 determines that target person P1 has body temperature abnormality (S307).

Abnormality determiner 133 subsequently generates alerting information to notify carer P2 of body temperature abnormality of target person P1 and causes third transmitter 135 to transmit the alerting information (S308).

In another case where the body temperature calculated in step S305 is less than the value acquired by adding the certain degree to the normal body temperature in the specific state stored in memory unit 134 (NO in S306), the processing flow proceeds to step S309.

History data management unit 136 subsequently accumulates the body temperature calculated in step S305 as history data in memory unit 134 (S309). In a case where a certain number of history data has been accumulated after last update of normal body temperature or where a certain period has elapsed after the last update of normal body temperature (YES in S310), reference body temperature management unit 137 calculates normal body temperature of target person P1 from the accumulated history data (S311). Reference body temperature management unit 137 subsequently updates the normal body temperature currently stored in memory unit 134 to the calculated normal body temperature (S312). When processing in step S312 ends, the processing flow returns to step S301.

In another case where the certain number of history data has not been accumulated after the last update of normal body temperature or where a certain period has not yet elapsed after the last update of normal body temperature (NO in S310), reference body temperature management unit 137 causes the processing flow to return to step S301.

As described above, abnormality notification system 1 according to the first exemplary embodiment compares reference body temperature for the specific state with body temperature indicated by thermal image data measured by second sensor 120 when target person P1 is determined as being in the specific state in accordance with active mass data measured by first sensor 110. It is thus determined whether or not target person P1 has body temperature abnormality. Abnormality notification system 1 accordingly achieves accurate detection of body temperature abnormality of a sensing target person in consideration of body temperature varying in accordance with states.

Second Exemplary Embodiment

Figure 4:
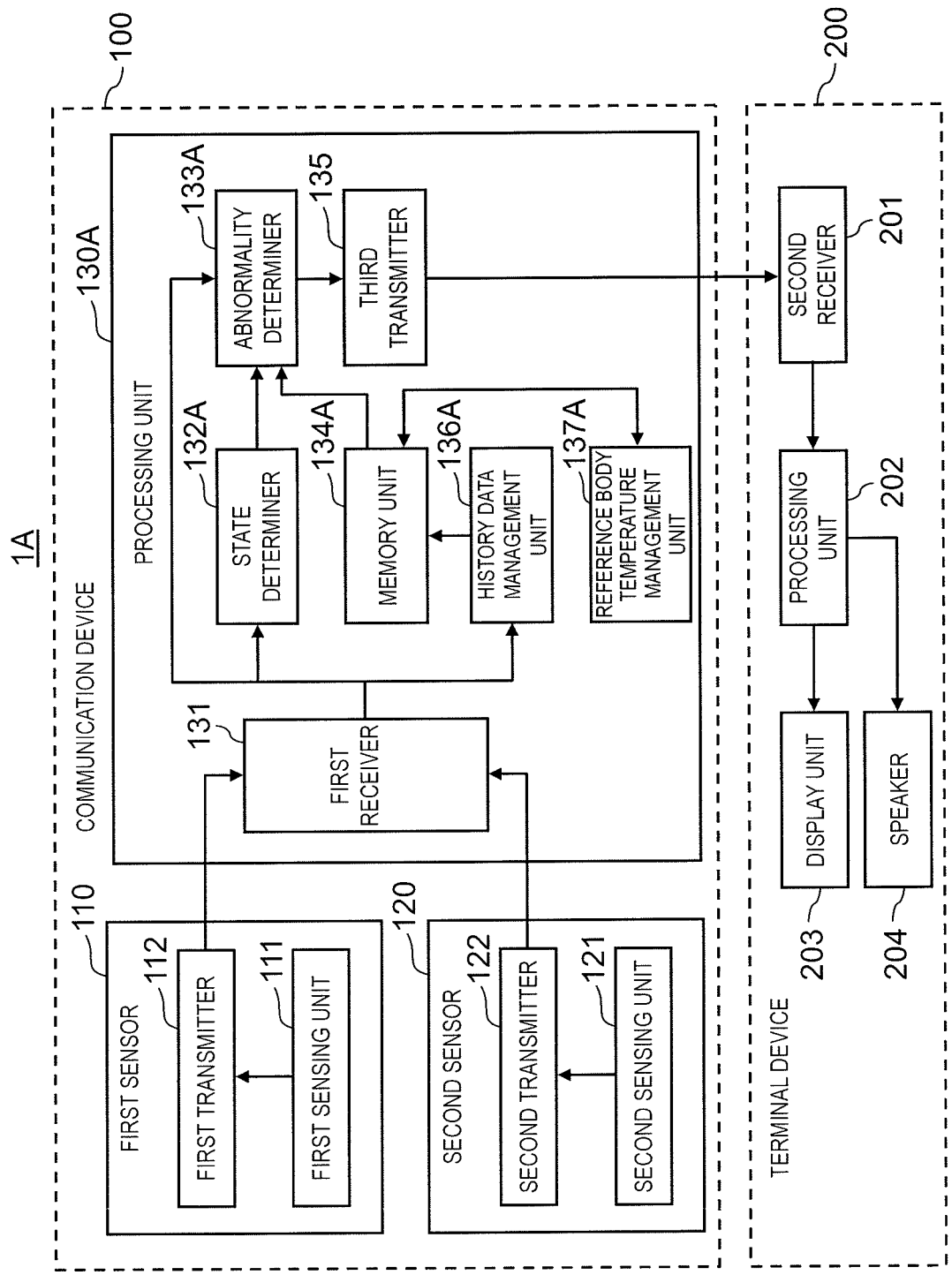
FIG. 4 is a block diagram depicting an entire configuration of an abnormality notification system according to a second exemplary embodiment of the present disclosure.

FIG. 4 is a block diagram depicting an entire configuration of abnormality notification system 1A according to the second exemplary embodiment.

Abnormality notification system 1A according to the second exemplary embodiment includes memory unit 134A configured to store normal body temperature values for a plurality of specific states. In the present exemplary embodiment, constituent elements identical to those according to the first exemplary embodiment will be denoted by identical reference marks and will not be described repeatedly.

FIG. 4 depicts constituent elements that are named identically with those according to the first exemplary embodiment but function differently. Such constituent elements each have symbol A at the end of the reference marks denoted in the first exemplary embodiment.

State determiner 132A determines in which one of preliminarily set specific states (exemplifying a plurality of predetermined states) target person P1 is in accordance with the active mass data measured by first sensor 110. Adoptable examples of the plurality of specific states include the state immediately after rising, the sleeping state, the eating state, and the state immediately before resting. The adoptable examples may further include a reading state, a state of watching TV, and a state of executing handwork.

State determiner 132A determines that target person P1 is in the sleeping state in an exemplary case where the active mass data has feature quantity similar to preliminarily set feature quantity for the sleeping state. State determiner 132A determines that target person P1 is in the eating state if the active mass data has feature quantity similar to preliminarily set feature quantity for the eating state, and determines that target person P1 is in the state immediately before resting if the active mass data has feature quantity similar to preliminarily set feature quantity for the state immediately before resting.

When state determiner 132A determines that target person P1 is in any one of the plurality of specific states, abnormality determiner 133A reads normal body temperature for the single specific state from memory unit 134A. Abnormality determiner 133A compares the read normal body temperature with the body temperature of target person P1 indicated by the thermal image data measured by second sensor 120 to determine whether or not target person P1 has body temperature abnormality.

Memory unit 134A stores normal body temperature for each of the plurality of specific states.

Figure 5:
FIG. 5 is a chart indicating a data configuration of a normal body temperature table including registered normal body temperature and stored in a memory unit according to the present disclosure.

FIG. 5 is a chart indicating a data configuration of normal body temperature table T1 including registered normal body temperature stored in memory unit 134A.

Normal body temperature table T1 includes normal body temperature ($T\_11$, $T\_12$, $T\_14$, $T\_15$) for the specific states, namely, "immediately after rising", "sleeping", "eating", and "immediately before resting", respectively.

Exemplarily assume that state determiner 132A determines that target person P1 is currently in the state of "immediately after rising". In this case, abnormality determiner 133A acquires normal body temperature $T\_11$ for the state of "immediately after rising" from memory unit 134A, and compares normal body temperature T_11 with current body temperature of target person P1. It is thus determined whether or not target person P1 has body temperature abnormality.

When the active mass data measured by first sensor 110 indicates that target person P1 is in any one of the plurality of specific states, history data management unit 136A generates history data including the single specific state associated with the body temperature of target person P1 acquired from the thermal image data measured by second sensor 120, and accumulates the history data in memory unit 134A.

Figure 6:
FIG. 6 is a chart indicating an exemplary data configuration of a history table including registered history data accumulated in the memory unit according to the present disclosure.

FIG. 6 is a chart indicating an exemplary data configuration of history table T2 including registered history data accumulated in memory unit 134A.

History table T2 is constituted by a database including each record associated with single registered history data, and has fields of "time", "specific state", and "body temperature".

The field "time" stores time of registration of history data in memory unit 134A. The time in this case has a data structure of year/month/time. The field "specific state" stores the specific state of target person P1 upon registration of history data. The field "body temperature" stores body temperature of the target person upon registration of history data.

FIG. 6 exemplifies a case where the active mass data indicates that target person P1 is in the state immediately after rising and the thermal image data indicates that target person P1 has body temperature at T01 degrees at 04:30 on Jan. 1, 2017. The fields "time", "specific state", and "body temperature" store "2017 Jan. 1/04:30", "immediately after rising", and "T01", respectively.

Reference body temperature management unit 137A refers to history table T2 accumulated in memory unit 134A, sorts body temperature values in the history data by the specific states, and calculates an average value of the body temperature for each of the specific states. Reference body temperature management unit 137A calculates normal body temperature for each of the plurality of specific states, and stores the calculated normal body temperature in memory unit 134A. This establishes normal body temperature table T1 indicated in FIG. 5. History table T2 indicated in FIG. 6 exemplifies a case where reference body temperature management unit 137A sorts the history data by the specific states including "immediately after rising", "eating", and "immediately before resting", and calculates an average value of body temperature from the sorted history data. This achieves calculation of normal body temperature for each of the specific states.

Reference body temperature management unit 137A has timing for calculation of normal body temperature, and variation of a range of the history data referred to for calculation of normal body temperature. Such timing and variation are the same as those according to the first exemplary embodiment.

Figure 7:
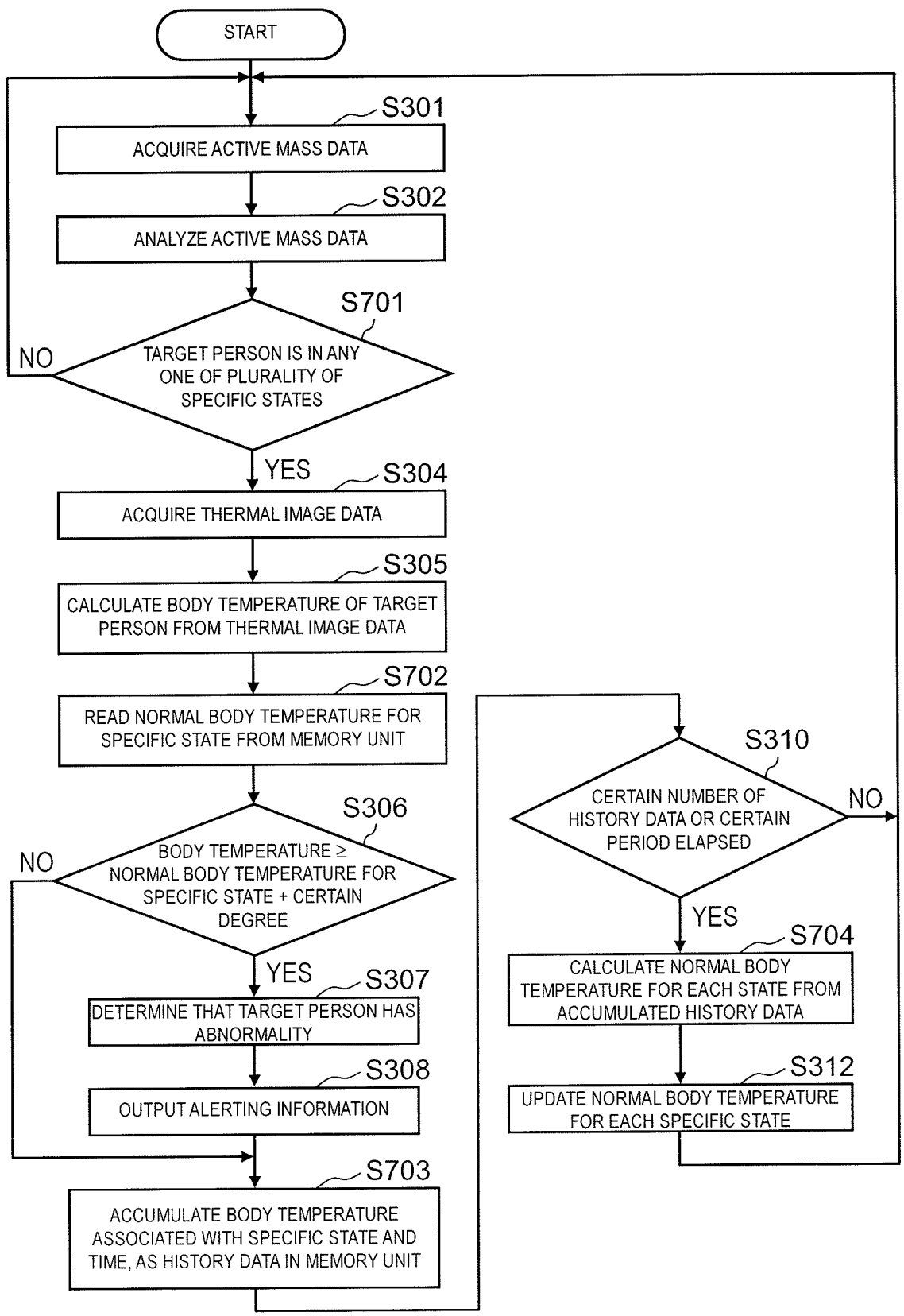
FIG. 7 is a flowchart depicting processing executed by the abnormality notification system according to the second exemplary embodiment of the present disclosure.

FIG. 7 is a flowchart depicting processing executed by abnormality notification system 1A according to the second exemplary embodiment. FIG. 7 includes processing steps same as those depicted in FIG. 3 and denoted by same processing numbers. Such processing steps will not be described repeatedly.

In step S701 subsequent to step S302, state determiner 132A determines whether or not target person P1 is in any one of the plurality of specific states. If target person P1 is not in any one of the specific states (NO in S701), the processing flow returns to S301. If target person P1 is in any one of the specific states (YES in S701), the processing flow proceeds to S304.

In step S702 subsequent to step S305, abnormality determiner 133A reads, from memory unit 134A, normal body temperature for the single specific state determined in step S701.

In step S703 subsequent to step S308, history data management unit 136A associates the single specific state determined in step S701 with the body temperature of target person P1 calculated in step S305 and current time to generate history data, and accumulates the history data in memory unit 134A. History table T2 indicated in FIG. 6 thus includes history data registered sequentially.

In step S704 subsequent to the case of YES in step S310, reference body temperature management unit 137A sorts the history data stored in history table T2 indicated in FIG. 6 by the specific states, and calculates an average value of body temperature for each history data thus sorted. This achieves calculation of normal body temperature for each of the specific states. Reference body temperature management unit 137A subsequently updates the normal body temperature for each of the specific states currently stored in memory unit 134A to the normal body temperature calculated for each of the specific states (S312).

Abnormality notification system 1A according to the second exemplary embodiment determines whether or not target person P1 has body temperature abnormality if target person P1 is in any one of plurality of the specific states. This configuration more precisely monitors whether or not target person P1 has body temperature abnormality. Normal body temperature table T1 stores normal body temperature for each of the plurality of specific states, to enable accurate detection of whether or not target person P1 has body temperature abnormality.

Third Exemplary Embodiment

The third exemplary embodiment provides abnormality notification system 1B configured to turn ON second sensor 120 only in a case where first sensor 110 detects target person P1.

In the present exemplary embodiment, constituent elements identical to those according to the first or second exemplary embodiment will be denoted by identical reference marks and will not be described repeatedly.

The present exemplary embodiment adopts the entire configuration depicted in FIG. 2 according to the first exemplary embodiment. The present exemplary embodiment may alternatively adopt the entire configuration depicted in FIG. 4 according to the second exemplary embodiment.

Figure 8:
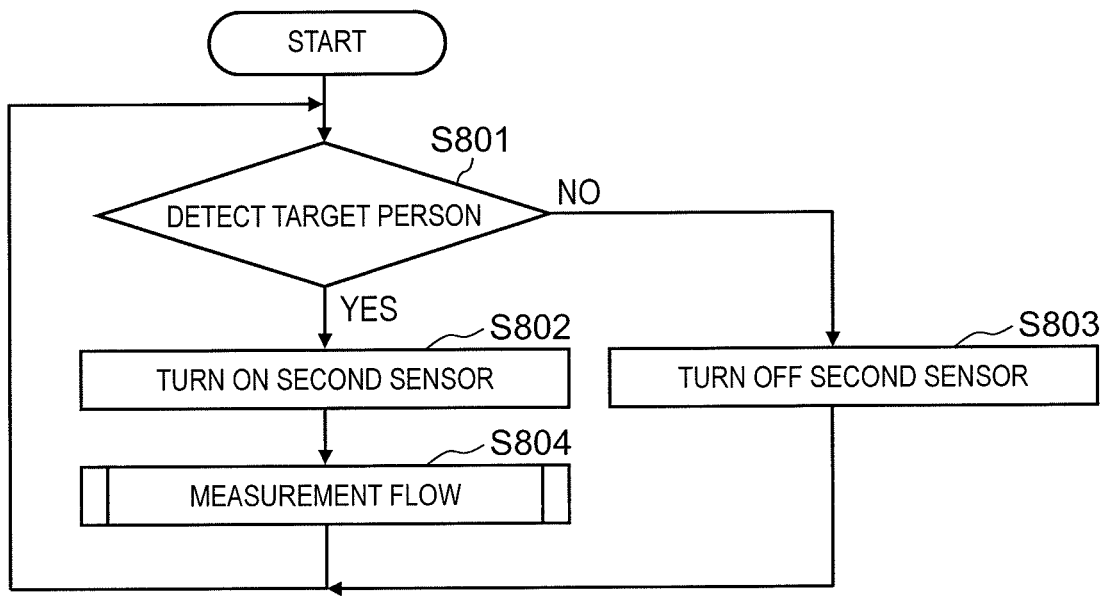
FIG. 8 is a flowchart depicting processing executed by an abnormality notification system according to a third exemplary embodiment of the present disclosure.

FIG. 8 is a flowchart depicting processing executed by abnormality notification system 1B according to the third exemplary embodiment.

Initially in step S801, state determiner 132 determines whether or not first sensor 110 has detected target person P1 in accordance with the active mass data acquired by first sensor 110.

In a case where the active mass data transmitted from first sensor 110 has a value more than or equal to a predetermined reference value indicating presence of target person P1, state determiner 132 determines that target person P1 is present.

State determiner 132 subsequently causes first receiver 131 to transmit, to second sensor 120, a control command to turn ON second sensor 120 in order to turn ON second sensor 120 (S802). If no target person is detected (NO in S801), the processing flow proceeds to step S803. In step S803, state determiner 132 causes first receiver 131 to transmit, to second sensor 120, a control command to turn OFF second sensor 120 in order to turn OFF second sensor 120. When processing in step S803 ends, the processing flow returns to step S801.

In step S804, abnormality notification system 1B executes a measurement flow and causes the processing flow to return to step S801. The measurement flow may follow the flowchart depicted in FIG. 3 and described in the first exemplary embodiment, or the flowchart depicted in FIG. 7 and described in the second exemplary embodiment.

In abnormality notification system 1B according to the third exemplary embodiment, second sensor 120 is started only in the case where target person P1 is present. This saves electricity consumption of second sensor 120. First sensor 110 is assumed to be constantly driven in the present exemplary embodiment.

Fourth Exemplary Embodiment

The fourth exemplary embodiment provides abnormality notification system 1C configured not to determine whether or not target person P1 has body temperature abnormality until a first period elapses if absence of target person P1 is detected and presence of target person P1 is then detected. Examples of the case of transition from absence to presence of target person P1 in the present exemplary embodiment include a case where target person P1 having been out returns to room R10.

In the present exemplary embodiment, constituent elements identical to those according to the first to third exemplary embodiments will be denoted by identical reference marks and will not be described repeatedly. The present exemplary embodiment adopts the entire configuration depicted in FIG. 2 according to the first exemplary embodiment. The present exemplary embodiment may alternatively adopt the entire configuration depicted in FIG. 4 according to the second exemplary embodiment.

Figure 9:
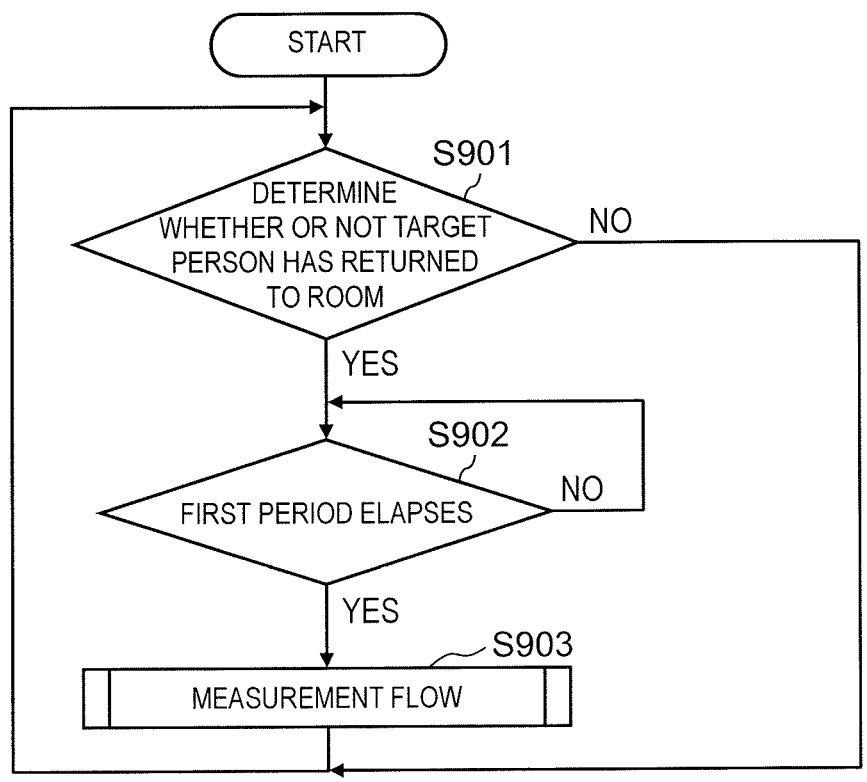
FIG. 9 is a flowchart depicting processing executed by an abnormality notification system according to a fourth exemplary embodiment of the present disclosure.

FIG. 9 is a flowchart depicting processing executed by abnormality notification system 1C according to the fourth exemplary embodiment.

State determiner 132 initially determines whether or not target person P1 has returned to room R10 (S901). If the active mass data transmitted from first sensor 110 is detected to have change from a value less than the predetermined reference value to a value more than or equal to the reference value indicating presence of target person P1, state determiner 132 determines that target person P1 has returned to room R10.

If target person P1 is determined as having returned to room R10 (YES in S901), abnormality determiner 133 determines whether or not the first period has elapsed (S902). Adoptable examples of the first period include a period expected to be needed for active mass of target person P1 to return to normal active mass. If the first period has not elapsed (NO in S902), the processing flow returns to step S902.

In step S903, abnormality notification system 1C executes a measurement flow and causes the processing flow to return to step S901. The measurement flow may follow the flowchart depicted in FIG. 3 and described in the first exemplary embodiment, or the flowchart depicted in FIG. 7 and described in the second exemplary embodiment.

Abnormality notification system 1C according to the fourth exemplary embodiment does not determine whether or not target person P1 has body temperature abnormality in a state where active mass is higher than normal active mass immediately after target person P1 returns into the room, to prevent erroneous detection of body temperature abnormality of target person P1.

Fifth Exemplary Embodiment

The fifth exemplary embodiment provides abnormality notification system 1D configured not to determine whether or not target person P1 has body temperature abnormality during a second period immediately after target person P1 receives a specific nursing care service.

In the present exemplary embodiment, constituent elements identical to those according to the first to fourth exemplary embodiments will be denoted by identical reference marks and will not be described repeatedly. Communication device 100 and terminal device 200 according to the present exemplary embodiment adopt the configurations depicted in FIG. 2 according to the first exemplary embodiment. Communication device 100 and terminal device 200 may alternatively adopt the configurations depicted in FIG. 4 according to the second exemplary embodiment.

Figures 10, 11:
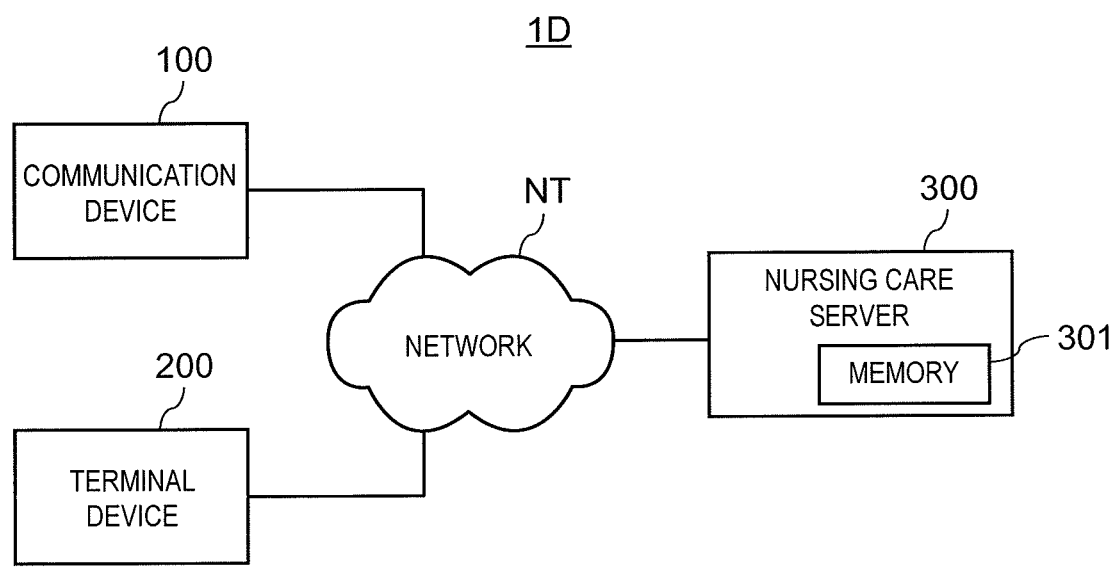
FIG. 10 is a diagram depicting an entire configuration of an abnormality notification system according to a fifth exemplary embodiment of the present disclosure.
FIG. 11 is a chart indicating a data configuration of a nursing care service history table according to the present disclosure.

FIG. 10 is a block diagram depicting an entire configuration of abnormality notification system 1D according to the fifth exemplary embodiment. Abnormality notification system 1D includes communication device 100 and terminal device 200 connected to nursing care server 300 via network NT. Adoptable examples of network NT include a public communication network such as the Internet.

Nursing care server 300 is constituted by a computer including a processor, a communication circuit, and the like, and is configured to record a history of a nursing care service received by target person P1. Nursing care server 300 is managed by a nursing care service provider who provides target person P1 with the nursing care service. Adoptable examples of the nursing care service provider include a facility provider described with reference to FIG. 1. If room R10 is located in the house of target person P1, the nursing care service provider may be a provider of at-home nursing care services.

Nursing care server 300 includes memory 301. Memory 301 may be constituted by a nonvolatile memory device, and stores nursing care service history table T3 indicated in FIG. 11.

FIG. 11 is a chart indicating a data configuration of nursing care service history table T3. Nursing care service history table T3 is constituted by a database including each record associated with registered history data on a single nursing care service, and has fields of "period" and "details of nursing care service".

The field "period" stores a period of the nursing care service received by target person P1. The field "details of nursing care service" stores details of a nursing care service received by target person P1. Adoptable examples of the details of a nursing care service include a bathing service of assisting target person P1 with bathing by carer P2, and an exercising service of assisting target person P1 with exercising by carer P2. The details of nursing care services are merely exemplarily indicated in FIG. 11, and other nursing care services may be registered where appropriate.

For example, target person P1 received a bathing service from 17:00 to 18:00 on Jan. 1, 2017, so that FIG. 11 has a first record including "2017 Jan. 1/17:00-18:00" and "bathing service".

Figure 12:
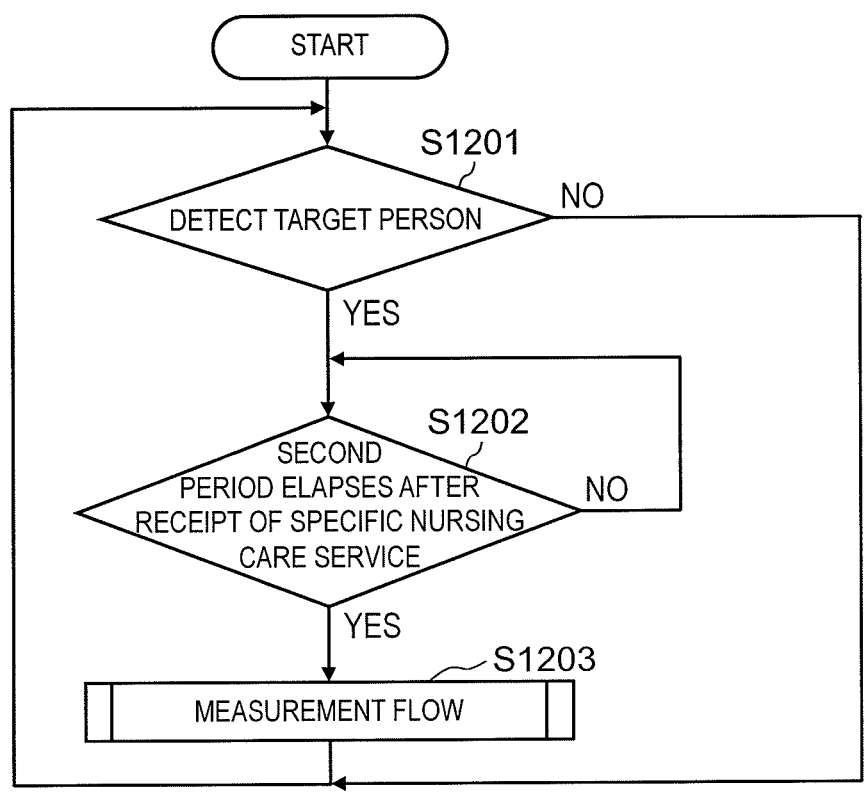
FIG. 12 is a flowchart depicting processing executed by the abnormality notification system according to the fifth exemplary embodiment of the present disclosure.

FIG. 12 is a flowchart depicting processing executed by abnormality notification system 1D according to the fifth exemplary embodiment.

Initially in step S1201, state determiner 132 determines whether or not first sensor 110 has detected target person P1 in accordance with the active mass data acquired by first sensor 110. Details of this processing are similar to those of the processing in step S801 depicted in FIG. 8.

Abnormality determiner 133 subsequently refers to nursing care service history table T3 indicated in FIG. 11 and determines whether or not the second period has elapsed after target person P1 received the specific nursing care service (S1202). The specific nursing care service in this case increases active mass of target person P1 and needs a certain period to return the active mass of target person P1 to normal active mass after the nursing care service ends. Examples of the specific nursing care service include the bathing service and the exercising service. Adoptable examples of the second period include a period expected to be needed for active mass of target person P1 to return to normal active mass after the nursing care service ends.

If the second period has not elapsed after receipt of the specific nursing care service (NO in S1202), the processing flow returns to step S1202. If the second period has elapsed after receipt of the specific nursing care service (YES in S1202), the processing flow proceeds to step S1203.

In step S1203, abnormality notification system 1D executes a measurement flow and causes the processing flow to return to step S1201. The measurement flow may follow the flowchart depicted in FIG. 3 and described in the first exemplary embodiment, or the flowchart depicted in FIG. 7 and described in the second exemplary embodiment.

Abnormality notification system 1D according to the fifth exemplary embodiment does not determine whether or not target person P1 has body temperature abnormality in a state where active mass is higher than normal active mass immediately after target person P1 receives the specific nursing care service, to prevent erroneous detection of body temperature abnormality of target person P1.

Sixth Exemplary Embodiment

The sixth exemplary embodiment provides abnormality notification system 1E configured to determine whether or not target person P1 is in the specific state with reference to time of acquisition of the active mass data as well as the active mass data.

In the present exemplary embodiment, constituent elements identical to those according to the first to fifth exemplary embodiments will be denoted by identical reference marks and will not be described repeatedly. The present exemplary embodiment adopts the entire configuration depicted in FIG. 4 according to the second exemplary embodiment. The present exemplary embodiment may alternatively adopt the entire configuration depicted in FIG. 2 according to the first exemplary embodiment.

State determiner 132A determines whether or not target person P1 is in any one of the plurality of specific states in accordance with the active mass data transmitted from first sensor 110, as in the first exemplary embodiment. State determiner 132A subsequently determines that the single specific state thus determined is true if the time of acquisition of the active mass data is included in a time zone preliminarily set for the single specific state thus determined. State determiner 132A determines that the determined state is false if the time of acquisition of the active mass data is not included in the time zone preliminarily set for the single specific state thus determined.

In an exemplary case where target person P1 is determined as being in the state immediately after rising during a time zone other than morning time, such a determination result is highly possibly false. In order to prevent such a situation, state determiner 132A is configured to execute the above processing.

More specifically, state determiner 132A includes a state determination table preliminarily setting a time zone enabling determination as being true for each of the specific states, and determines whether the specific state determined in accordance with the active mass data is true or false with reference to the state determination table.

Abnormality notification system 1E according to the sixth exemplary embodiment determines whether or not target person P1 is in the specific state in further consideration of time of acquisition of the active mass data. This enables more accurate detection of whether or not target person P1 is in the specific state.

Seventh Exemplary Embodiment

The seventh exemplary embodiment provides abnormality notification system IF configured to detect target person P1 out of a plurality of persons detected in accordance with the thermal image data.

In the present exemplary embodiment, constituent elements identical to those according to the first to fifth exemplary embodiments will be denoted by identical reference marks and will not be described repeatedly. The present exemplary embodiment adopts the entire configuration depicted in FIG. 2 according to the first exemplary embodiment. The present exemplary embodiment may alternatively adopt the entire configuration depicted in FIG. 4 according to the second exemplary embodiment.

Memory unit 134 preliminarily stores positional information indicating a position of target person P1 staying in the measurement range around second sensor 120.

FIG. 1 exemplarily adopts a region provided with bed 103 as a position where target person P1 stays. FIG. 1 assumes that bed 103 is positioned in the measurement range of second sensor 120. Adoptable examples of the positional information include coordinates data indicating the region provided with bed 103 in the thermal image data captured by second sensor 120.

Abnormality determiner 133 determines that the thermal image data includes a plurality of persons in an exemplary case of detecting a plurality of regions each having a silhouette of a person in the thermal image data.

If the plurality of persons is detected in the thermal image data and the plurality of persons thus detected includes any person having the region of the silhouette overlapped with a region indicated by the positional information, abnormality determiner 133 determines that the person corresponds to target person P1.

Abnormality determiner 133 may alternatively detect target person P1 in consideration of movement of each person. In an exemplary case where abnormality determiner 133 determines that a plurality of persons is present in accordance with the thermal image data, abnormality determiner 133 follows movement of each of the persons for a certain period and acquires length of a movement locus of each of the persons in accordance with the thermal image data. The plurality of detected persons will include, in addition to target person P1, a person visiting target person P1, carer P2, and the like. The visiting person and carer P2 are thus assumed to move more actively than target person P1.

In view of this, abnormality determiner 133 determines that target person P1 corresponds to the person having the shortest movement locus out of a plurality of persons each having a silhouette region overlapped with the region indicated by the positional information.

Abnormality determiner 133 may determine that target person P1 corresponds to the person having the shortest movement locus if a plurality of persons is detected and there is no person having the silhouette region overlapped with the region indicated by the positional information. Abnormality determiner 133 may alternatively determine that target person P1 corresponds to the person having the shortest movement locus in no consideration of the positional information.

The measurement range of second sensor 120 may include a plurality of target persons P1. In this case, abnormality determiner 133 preliminarily stores, in memory unit 134, positional information on the plurality of target persons P1 associated with identifiers of the target persons P1. Abnormality determiner 133 specifies target person P1 in accordance with the identifier associated with the positional information on the region overlapped with the silhouette region and extracted from the thermal image data in a plurality of regions indicated by a plurality of positional information.

The present disclosure can adopt the following modification examples.

(1) FIG. 2 exemplifies processing unit 130 including history data management unit 136 and reference body temperature management unit 137, which may not be provided in the present disclosure. In this case, memory unit 134 may store preliminarily set normal body temperature in place of normal body temperature calculated from history data.

(2) FIG. 4 exemplifies processing unit 130A including history data management unit 136A and reference body temperature management unit 137A, both of which may not be provided in the present disclosure. In this case, memory unit 134A may store preliminarily set normal body temperature for each state in place of normal body temperature for each state calculated from history data.

(3) The above description refers to first sensor 110 constituted by a radio wave sensor. The present disclosure is not limited to this case, and first sensor 110 may be constituted by any other sensor configured to measure active mass of target person P1. For example, first sensor 110 may be constituted by a sensor configured to measure a heart rate or a brain wave. In this case, state determiner 132 detects a state of target person P1 in accordance with the heart rate or the brain wave. Furthermore, first sensor 110 is described as a contactless sensor. The present disclosure is not limited to this case, and first sensor 110 may be constituted by a contact sensor.

(4) The above description exemplarily refers to second sensor 120 constituted by a thermal image sensor, but second sensor 120 may be constituted by any other sensor configured to measure body temperature of target person P1. For example, second sensor 120 may be constituted by a contact thermometer.

INDUSTRIAL APPLICABILITY

The present disclosure significantly achieves accurate detection of body temperature abnormality of a sensing target person. The present disclosure is thus usefully applicable to a communication device, an abnormality notification system, an abnormality notification method, and the like in a technical field of watching a nursed person and the like.

REFERENCE MARKS IN THE DRAWINGS

T1: normal body temperature table
T2: history table
T3: nursing care service history table
1, 1A, 1B, 1C, 1D, 1E, 1F: abnormality notification system
100: communication device
110: first sensor
111: first sensing unit
112: first transmitter
120: second sensor
121: second sensing unit
122: second transmitter
130, 130A: processing unit
131: first receiver
132, 132A: state determiner
133, 133A: abnormality determiner
134, 134A: memory unit
135: third transmitter
136, 136A: history data management unit
137, 137A: reference body temperature management unit
200: terminal device
201: receiver
202: processing unit
203: display unit
204: speaker
300: nursing care server
301: memory

The invention claimed is:

1. A communication device configured to notify of abnormality of a sensing target person, the communication device comprising:
a first sensor configured to measure an activity state of the sensing target person to acquire first measurement data;
a second sensor configured to measure a body temperature of the sensing target person to acquire second measurement data;
a memory unit configured to store a reference body temperature of the sensing target person for a plurality of activity states of the sensing target person;
a state determiner configured to determine whether or not the sensing target person is in one of the plurality of activity states in accordance with the first measurement data acquired by the first sensor; and
an abnormality determiner configured to, when the state determiner determines that the sensing target person is in the one of the plurality of activity states, compare the reference body temperature corresponding to the one of the plurality of activity states with the body temperature of the sensing target person indicated by the second measurement data acquired by the second sensor, to determine whether or not the sensing target person has a body temperature abnormality; wherein
when the abnormality determiner determines that the sensing target person has the body temperature abnormality, the abnormality determiner generates alerting information for notification of the body temperature abnormality, and
the second sensor is a thermal image sensor.

2. The communication device according to claim 1, wherein
the first sensor and the second sensor periodically acquire the first measurement data and the second measurement data, respectively,
the communication device further comprises:
a history data management unit configured to generate, when the first measurement data acquired by the first sensor indicates that the sensing target person is in the one of the activity states, history data including the body temperature of the sensing target person acquired from the second measurement data and the one of the plurality of activity states associated with each other, and accumulate the history data in the memory unit; and a reference body temperature management unit configured to analyze the history data, calculate the reference body temperature for the one of the plurality of activity states, and store the reference body temperature in the memory unit.

3. The communication device according to claim 2, wherein the reference body temperature management unit analyzes the history data, calculates, as the reference body temperature, a normal body temperature of the sensing target person for the one of the plurality of activity states, and stores the normal body temperature in the memory unit, and the abnormality determiner determines that the sensing target person has the body temperature abnormality when the body temperature of the sensing target person is higher than the normal body temperature for the one of the plurality of activity states by at least a certain degree.

4. The communication device according to claim 1, wherein the first sensor is a radio wave sensor, and the second sensor is a thermal image sensor.

5. The communication device according to claim 1, wherein the first sensor measures active mass of the sensing target person.

6. The communication device according to claim 1, wherein the state determiner determines whether or not the sensing target person is in the one of the plurality of activity states in accordance with the first measurement data and time of acquisition of the first measurement data.

7. The communication device according to claim 1, wherein the state determiner detects whether or not the sensing target person is present in accordance with the first measurement data acquired by the first sensor, and the abnormality determiner starts the second sensor only in a case where the state determiner detects presence of the sensing target person.

8. The communication device according to claim 1, wherein the state determiner detects whether or not the sensing target person is present in accordance with the first measurement data acquired by the first sensor, and when the state determiner detects absence of the sensing target person and then detects presence of the sensing target person, the abnormality determiner does not determine whether or not the sensing target person has the body temperature abnormality until a first period elapses after detection.

9. The communication device according to claim 1, wherein the sensing target person is a nursed person who receives a nursing care service, the communication device is connected to a nursing care server configured to record a history of the nursing care service received by the nursed person via a network, and the abnormality determiner determines whether or not a second period has elapsed after the nursed person receives the nursing care service with reference to the history of the nursing care service, and does not determine whether or not the nursed person has the body temperature abnormality until the second period elapses.

10. The communication device according to claim 1, wherein the second sensor is a thermal image sensor configured to measure, as the first measurement data, thermal image data indicating temperature distribution in a measurement range around the second sensor, the memory unit preliminarily stores positional information indicating a position of the sensing target person staying in the measurement range, and when a plurality of persons is detected in the measurement range in accordance with the thermal image data, the abnormality determiner compares coordinates of each of the persons in the thermal image data with the positional information to determine which one of the plurality of persons corresponds to the sensing target person.

11. An abnormality notification system configured to notify of abnormality of a sensing target person, the abnormality notification system comprising:

the communication device according to claim 1; and a terminal device connected to the communication device via a network; wherein the terminal device includes an output unit configured to output alerting information generated by the abnormality determiner in the communication device.

12. The communication device according to claim 1, wherein the plurality of activity states includes the states of (a) immediately after rising, (b) sleeping, (c) eating, (d) immediately before resting, (e) reading, (f) watching TV, and (g) executing handwork.

13. The communication device according to claim 1, wherein the first sensor is a radio wave sensor.

14. The communication device according to claim 1, wherein the first sensor is a radio wave sensor configured to emit a radio wave and to receive the radio wave reflected from the target person.

15. The communication device according to claim 1, wherein the first sensor is a radio wave sensor configured to emit a radio wave and to receive the radio wave reflected from the target person, and detect a frequency change of the emitted radio wave and the reflected wave caused in accordance with a moving speed of target person, and acquire active mass data indicating the active mass of the target person from the frequency change thus detected.

16. The communication device according to claim 1, wherein the first sensor is a radio wave sensor configured to emit a radio wave and to receive the radio wave reflected from the target person, and comprises a frequency modulated continuous wave system.

17. The communication device according to claim 1, wherein the first sensor is a contactless sensor.

18. An abnormality notification method with use of an abnormality notification system configured to notify of abnormality of a sensing target person, the abnormality notification method comprising:

(a) measuring an activity state of the sensing target person to acquire first measurement data with use of a first sensor, the activity state being one of a plurality of activity states;

(b) measuring a body temperature of the sensing target person to acquire second measurement data with use of a second sensor;

(c) determining whether or not the sensing target person is in one of the plurality of activity states in accordance with the first measurement data acquired by the first sensor; and (d) comparing the reference body temperature for the one of the plurality of activity states preliminarily stored in a memory unit with the body temperature of the sensing target person indicated by the second measurement data acquired by the second sensor, when the sensing target person is determined as being in the one of the plurality of activity states, to determine whether or not the sensing target person has the body temperature abnormality;

(e) generating, when the body temperature of the sensing target person is determined as having the body temperature abnormality, alerting information for notification of the body temperature abnormality; and (f) outputting the generated alerting information, wherein the second sensor is a thermal image sensor.

19. The abnormality notification method according to claim 18, wherein the plurality of activity states includes the states of (a) immediately after rising, (b) sleeping, (c) eating, (d) immediately before resting, (e) reading, (f) watching TV, and (g) executing handwork.

* * * * *